United States Patent [19]
Caughman et al.

[11] 3,993,777
[45] Nov. 23, 1976

[54] AQUEOUS COMPOSITIONS TO AID IN THE PREVENTION OF BOVINE MASTITIS

[75] Inventors: Henry Daniel Caughman, Lithonia; William Edgar Brown, Conyers, both of Ga.

[73] Assignee: Bio-Lab, Inc., Decatur, Ga.

[22] Filed: Aug. 12, 1975

[21] Appl. No.: 603,947

[52] U.S. Cl. .................................. 424/329
[51] Int. Cl.² ............................. A61K 31/14
[58] Field of Search ........................ 424/329

[56] References Cited
UNITED STATES PATENTS

| | | | |
|---|---|---|---|
| 3,250,681 | 5/1966 | Zbornik et al. | 424/362 |
| 3,251,824 | 5/1966 | Battista | 424/362 |
| 3,347,743 | 10/1967 | Reuter et al. | 424/329 |
| 3,639,623 | 2/1972 | Ritschel et al. | 424/329 |
| 3,830,920 | 8/1974 | Morrison et al. | 424/329 |

FOREIGN PATENTS OR APPLICATIONS

| | | |
|---|---|---|
| 1,184,200 | 3/1970 | United Kingdom |

*Primary Examiner*—Sam Rosen
*Attorney, Agent, or Firm*—Walter M. Rodgers; Walter A. Rodgers

[57] ABSTRACT

An aqueous composition is provided to aid in the prevention of mastitis in udders. The composition consists of:

| | Percent |
|---|---|
| Emollients | 0–10 |
| Surface active alkyl, quaternary ammonium germicides | 0.05–8.0 |
| Water dispersable coloring agent of food.grade | 0.0001–5.0 |
| Thickening agent | 0.1000–20.0 |
| Water | Balance |

2 Claims, No Drawings

AQUEOUS COMPOSITIONS TO AID IN THE PREVENTION OF BOVINE MASTITIS

BACKGROUND OF THE INVENTION

Mastitis is an infectious disease of the bovine udder caused by harmful micro-organisms entering the teat canal through the teat orifice and/or through lesions upon the surface of bovine udder quarters. Usual sources of harmful microbes include the milker, unsanitary milking equipment, other mastitic cows, an unsanitary environment and the cow's own eliminations and secretions. Annual pecuniary loss to this disease has been estimated to be in the hundreds of millions of dollars in the United States alone. Estimates of total annual milk product lost in the United States due to mastitis range from 10 to 25 percent.

In 1916, Moak proposed the practice of dipping cow teats in a germicidal solution immediately after milking; however, this has become a well spread practice in the dairy industry only in the last decade. This time lag has been most unfortunate for there is ample documentation in scientific and trade journals attesting to the fact that a post-milking teat-dipping program will significantly reduce the number of cases of mastitis.

Teat-dipping using a well balanced formulation accomplishes these essential functions: (1) Dipping removes the final drop of milk on the end of the teat. Unattended, this drop of milk is an excellent breeding media for infectious organisms. (2) Dipping in an effective sanitizing solution controls most organisms on the skin, reducing the number that may enter the teat canal. Among the organisms that are controlled are those that have been shown to cause mastitis. (3) Dipping in a balanced formulation aids in healing minor skin lesions and contributes to the overall health of the udder.

While there are a number of germicides that are effective in preventing and treating mastitis, most preparations have the disadvantage of only remaining in contact with the udder for a short time due to the mobility of the preparation. Longer contact time is desirable in order to insure a higher kill rate for the harmful bacteria.

While proper application of many dipping preparations will kill the harmful bacteria on the udder at the time of dipping, the majority of the bacterial invasions of the udder probably occur during the intermilking period. A dip preparation that formed a protective pliable film about the teat would reduce its susceptibility to dirt, bacteria and other foreign matter. Such a film would also form a bacteriostatic barrier about the teat, reducing the possibility of bacterial invasion. Certain oil based preparations, such as those disclosed in U.S. Pat. No. 3,222,252 will upon drying form a protective coating that will remain on the udder for some time. However, Philpot and Pankey, in the Journal of Dairy Science, Vol. 58, pp. 205–216, have shown that oil-based teat dipping preparations perform poorly in preventing mastitis infections and were shown to frequently increase the numbers of mastitis producing organisms. Secondarily, oil based preparations are not easily removed by washing prior to milking. It is desirable that such preparations be completely removed prior to milking to prevent any contamination of the milk by the preparation.

Because it is essential that the udders of all the cows in the herd be dipped after milking, an easy method of determining whether the cows have been treated is desirable. Complexed iodines, commonly termed "iodophors" have been employed as germicides in teat-dipping solutions for over a decade. They offer the advantage of being chromophoric. It is highly desirable to obtain this characteristic with other germicides.

THE INVENTION

We provide a composition having broadly the following composition:

| | Percent |
|---|---|
| Emollients | 0–10 |
| Surface active alkyl, quaternary ammonium germicides | 0.05–8.0 |
| Water dispersable coloring agent of food grade | 0.0001–5.0 |
| Thickening agent | 0.1000–20.0 |
| Water | Balance |

A typical preferred formulation is:

| | Percent |
|---|---|
| Ethoxylated lanolin | 2.50 |
| Glycerine | 3.00 |
| $C_{12}$–$C_{16}$ alkyl dimethyl benzyl ammonium chloride | 0.12 |
| $C_{12}$–$C_{16}$ alkyl dimethyl ethyl ammonium bromide | 0.02 |
| Water dispersable coloring agent of food grade | 0.07 |
| Hydroxyethylcellulose | 1.00 |
| Water | Balance |

Ethoxylated lanolin and glycerine are preferred as emollients and skin conditioners in the formulation. They replace some of the natural skin oil lost by the milking process and use of washing solutions. In addition, they assist in forming the protective coating on the skin. Other suitable emollients are isopropyl myristate; isopropyl palmitate; other similar esters; propylene glycol and its numerous derivatives; other glycol derivatives; vegetable oils; petroleum fractions; high molecular weight alcohols; allantoin and many others. Carriers other than water have also been employed. A list of these would include various nonionic surfactants, various anionic surfactants, various cationic surfactants and alcohols.

The alkyl dimethyl benzyl ammonium chloride and alkyl dimethyl ethyl ammonium bromide (quaternary ammonium halide) preferably are employed as germicides in the formulation. A typical alkyl dimethyl benzyl ammonium chloride is commercially supplied as a 50% solution in ethyl alcohol. A typical alkyl dimethyl benzyl ammonium bromide is commercially supplied as a 50% solution in an equal mixture of isopropyl alcohol and water. Other suitable surface active alkyl, quaternary ammonium germicides are alkyl ($C_8$–$C_{18}$) benzyldimethylammonium chloride, alkyl ($C_8$–$C_{18}$) benzyldimethylammonium bromide, alkyl ($C_8$–$C_{18}$) trimethylammonium chloride, alkyl ($C_8$–$C_{18}$) trimethylammonium bromide, alkyl ($C_8$–$C_{18}$) pryridinium chloride, alkyl ($C_8$–$C_{18}$) pryridinium bromide, alkyl ($C_8$–$C_{18}$) dimethylethylammonium chloride, alkyl ($C_8$–$C_{18}$) dimethylethylammonium bromide, dialkyl ($C_8$–$C_{18}$) dimethyl ammonium chloride, dialkyl ($C_8$–$C_{18}$) dimethyl ammonium bromide, alkyl ($C_8$–$C_{18}$) dimethyldichlorobenzylammonium chloride, alkyl ($C_8$–$C_{18}$) dimethyldichlorobenzylammonium bromide, alkyl ($C_8$–$C_{18}$) tolylmethyltrimethylammonium chloride, para-diisobutylphenoxyethoxyethyldimethylbenzylammonium chloride and para-diisobutylcresoxyethoxyethyldimethylbenzylammonium chloride.

The water soluble coloring agent serves to visually apprise the herdsmen that the cow's udder has been treated with the formulation. The coloring agent should be of food grade because of the possibility of accidental entry into the milk. It is important that the dye be water dispersable and easily washed from the udder prior to milking. Otherwise, the herdsmen would not know whether the formulation had been used after milking if the color from a prior application was retained on the udder. The dye should be of a color that will offer a sharp contrast to skin and farm background color tones.

A suitable coloring agent is purple lake blend. Other suitable coloring agents are carbon black dispersion, black lake, F.D. and C. (Federal Food Drug and Cosmetic Agency) blue number one, red number 3 lake, green number 3, yellow number 6 lake, and blue number 1 dye.

Hydroxyethylcellulose, employed as a thickening agent in the above preferred formulation, has the characteristic of forming pliable non-brittle films upon drying. The thickening agent also serves to produce a more heavily bodied retentive film which, when a dye is incorporated, renders the color more pronounced. Other thickening agents are gum arabic, gum tragacanth, gum karaya, gum larch, gum ghatti, locust bean gum, guar gum, phsyllium seed gum, quince seed gum, agar, algin, carrageenan, furcellaran, pectin, gelatin, other proteins, starch, carboxymethylcellulose, methylcellulose, hydroxypropylmethylcellulose, hydroxypropylcellulose, hydroxyethylcellulose, ethylhydroxyethylcellulose, carboxymethylstarch, hydroxyethylstarch, hydroxypropylstarch, dextran, polysaccharide B1459 (Kelzan), low methoxyl pectin, propylene glycol alginate, triethanolamine alginate, carboxymethyl locust bean gum, carboxymethyl guar gum, polyvinylpyrrolidone, polyvinylalcohol, carboxyvinyl polymer, polyacrylic acid and its derivatives, polyacrylamide and ethylene oxide polymers.

The preferred formulation is prepared by dissolving in the following order in most of the required water: ethoxylated lanolin, glycerine and the two commercial quaternary ammonium halides. The coloring agent is then mixed with the remaining water and added to the above mixture. Hydroxyethylcellulose is then slowly added while the mixture is being vigorously stirred. The entire mixture is then stirred for one hour.

This formulation is used undiluted as a teat-dipping solution. The preferred method of application is to pour a portion of the formulation into a small cup and dip each teat in turn into the cup.

The formulation of this invention offers a number of significant advantages over prior preparations. The viscosity of the formulation is sufficiently high, decreasing its mobility of the dipping liquid so that the contact time of the germicide on the skin surface is increased. This formulation also forms a protective pliable film about the teat, reducing its susceptibility to bacteria, dirt and other foreign matter. In addition, this film forms a bacteriostatic barrier about the teat.

Unlike the oil based films, this film is easily removed by washing. The addition of a coloring agent gives the formulation the color identification advantage of the iodophors with a germicide formulation which offers certain advantages over the iodophors.

The embodiments of the invention in which an exclusive property or privilege is claimed are defined as follows:

1. An aqueous composition for use as an aid in the prevention of bovine mastitis, comprising

| | Percent |
|---|---|
| Ethoxylated lanolin | 2.50 |
| Glycerine | 3.00 |
| $C_{12}$–$C_{16}$ alkyl dimethyl benzyl ammonium chloride | 0.12 |
| $C_{12}$–$C_{16}$ alkyl dimethyl ethyl ammonium chloride | 0.02 |
| Ethyl alcohol | 0.12 |
| Isopropyl alcohol | 0.01 |
| Water dispersable coloring agent of food grade | 0.07 |
| Hydroxyethylcellulose | 1.00 |
| Water | Balance |

2. An aqueous composition as claimed in claim 1 in which the water dispersable coloring agent of food grade is purple lake blend.

* * * * *

UNITED STATES PATENT AND TRADEMARK OFFICE
CERTIFICATE OF CORRECTION

PATENT NO. : 3,993,777
DATED : November 23, 1976
INVENTOR(S) : Henry Daniel Caughman, Lithonia;
William Edgar Brown, Conyers It is certified that error appears in the above-identified patent and that said Letters Patent are hereby corrected as shown below:

In claim 1, the portion of the composition following $C_{12}-C_{16}$ alkyl dimethyl ethyl reading "ammonium chloride" should read - ammonium bromide -

Signed and Sealed this

Seventh Day of July 1981

[SEAL]

Attest:

RENE D. TEGTMEYER

Attesting Officer     Acting Commissioner of Patents and Trademarks